US010869832B2

(12) United States Patent
Chen et al.

(10) Patent No.: US 10,869,832 B2
(45) Date of Patent: *Dec. 22, 2020

(54) SUBSTANCE DELIVERY DEVICE AND SUBSTANCE DELIVERY METHOD USING THE SAME

(71) Applicant: National Cheng Kung University, Tainan (TW)

(72) Inventors: Mei-Chin Chen, Tainan (TW); Zih-Yao Lin, Tainan (TW); Chia-Sui Chen, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 315 days.

This patent is subject to a terminal disclaimer.

(21) Appl. No.: 16/009,920

(22) Filed: Jun. 15, 2018

(65) Prior Publication Data

US 2018/0289616 A1   Oct. 11, 2018

Related U.S. Application Data

(63) Continuation-in-part of application No. 14/328,571, filed on Jul. 10, 2014, now Pat. No. 10,028,905.

(30) Foreign Application Priority Data

Jul. 12, 2013   (TW) .............................. 102125095 A

(51) Int. Cl.
*A61K 9/00* (2006.01)
*A61K 9/70* (2006.01)
(Continued)

(52) U.S. Cl.
CPC .......... *A61K 9/0021* (2013.01); *A61K 9/7084* (2013.01); *A61M 37/0015* (2013.01);
(Continued)

(58) Field of Classification Search
CPC .... A61K 9/0021; A61K 9/7084; A61K 41/00; A61K 47/32; A61M 37/0015
(Continued)

(56) References Cited

U.S. PATENT DOCUMENTS

2002/0082543 A1   6/2002   Park et al.
2008/0167601 A1   7/2008   Laermer et al.
(Continued)

OTHER PUBLICATIONS

"Transdermal Delivery of Active Ingredients with Dissolving Microneedles for Skin Depigmentation", http://www.airitilibrary.com/Publication/alDetailedMesh?docid;US0026-2608201321153000, 2 pages, Jan. 1, 2013.
(Continued)

*Primary Examiner* — Phillip A Gray
(74) *Attorney, Agent, or Firm* — Muncy, Geissler, Olds & Lowe, PC

(57) ABSTRACT

A substance delivery device comprises a substrate, a plurality of dissolvable supporting structures and a plurality of carriers. The substrate attaches to a tissue. The dissolvable supporting structures are disposed on the substrate. The carriers are disposed on the dissolvable supporting structures and encapsulating substances. The present invention further provides a substance delivery method. The substance delivery device and the substance delivery method of present invention is advantageous for providing sustained release effect and rising the applicability of transdermal or transmucosal delivery techniques.

17 Claims, 16 Drawing Sheets

(51) Int. Cl.
  *A61M 37/00* (2006.01)
  *A61K 41/00* (2020.01)
  *A61K 47/36* (2006.01)
  *A61K 47/32* (2006.01)

(52) U.S. Cl.
  CPC .............. *A61K 41/00* (2013.01); *A61K 47/32* (2013.01); *A61K 47/36* (2013.01); *A61M 2037/0023* (2013.01); *A61M 2037/0046* (2013.01)

(58) Field of Classification Search
  USPC .......................................................... 604/46
  See application file for complete search history.

(56) References Cited

U.S. PATENT DOCUMENTS

| | | | |
|---|---|---|---|
| 2008/0269685 A1* | 10/2008 | Singh | A61M 37/0015 604/173 |
| 2010/0228203 A1* | 9/2010 | Quan | A61M 37/0015 604/272 |
| 2011/0028905 A1 | 2/2011 | Takada | |
| 2013/0165902 A1 | 6/2013 | Stumber et al. | |
| 2014/0276589 A1* | 9/2014 | Bayramov | A61K 9/0021 604/506 |

OTHER PUBLICATIONS

M.-C. Chen et al., "Fully embeddable chitosan microneedles as a sustained release depot for intradermal vaccination," Biomaterials, 2013, pp. 3077-3086, vol. 34.

* cited by examiner

US 10,869,832 B2

SUBSTANCE DELIVERY DEVICE AND SUBSTANCE DELIVERY METHOD USING THE SAME

CROSS REFERENCE TO RELATED APPLICATIONS

This application is a Continuation-In-Part of U.S. application Ser. No. 14/328,571 filed on Jul. 10, 2014.

BACKGROUND OF THE INVENTION

Field of Invention

The present invention relates to a substance delivery device and a substance delivery device using the same.

Related Art

Oral administration and subcutaneous injection are general and traditional routes for delivering a drug. Oral administration is now a most widely used method to deliver a drug because of its convenience. However, oral administration and subcutaneous injection both have drawbacks.

Oral medications, after swallowed, are digested in the gastrointestinal system and pass through the liver to experience a first-pass metabolism, and emerge from the liver to enter the circulatory system, to such an extent that the remaining medications actually have systemic effect. The whole process not only costs much time, but includes other factors (e.g. digestion) which make it is difficult to control the efficacy of drugs precisely, and even make the drug lose its efficacy. On the other hand, subcutaneous injection of drugs is an invasive treatment which may not only be very painful, but also poses a risk of infection by needle.

Transdermal drug delivery (TDD) has become an attractive route to administer drugs in recent years. It is a route to deliver medications through skin and the medications will be absorbed thereby. The forms of TDD include ointment, oil, patch, gel, and inhalation aerosol. TDD not only avoids the possibility to lose the efficacy of medication resulted from digestion of gastrointestinal system as oral medications do, but also has advantages over subcutaneous injections, which are painful and pose the risk of infection.

However, stratum corneum is the outermost protective layer of skin. It is hydrophobic and negatively charged, which poses particular challenges in delivery of macromolecules and hydrophilic drugs through skin.

In order to overcome the abovementioned difficulties, in recent years, a technique has been developed to combine a traditional needle-injection and a transdermal drug delivery patch, which has been accomplished by covering a patch with microneedles. Microneedles can penetrate the stratum corneum to directly deliver macromolecular drugs and hydrophilic drugs, such as vaccines, proteins, insulin, and deoxyribonucleic acids, to epidermis and dermis. Therefore, drugs will be absorbed through capillaries and then enter into systemic circulation. Transdermal drug delivery with a microneedle patch has advantages over the traditional needle-injection TDD can reduce discomforts significantly and patients may therefore have a higher intention to take vaccination. The microneedle patch is a gospel to those who fear of traditional needle-injection, especially children and even elderly. In addition, a microneedle patch is easy for medical personnel and patients to handle it conveniently.

However, current techniques focus on developing microneedle patches which can release substances, such as vaccines and drugs, in a short-term, and are rapid-release forms. A few sustained-release patches use bio-degradable polymer as the material of microneedles. However, such patches have to be placed on skin for quite a long time to reach a sustained release. It often induces allergic reactions, such as symptoms of itching and skin rashness, and causes patients' discomfort and inconvenience.

Therefore, it is an important subject to provide a substance delivery device and method providing a sustained release without bringing patients discomfort by improving materials, structures and release process.

SUMMARY OF THE INVENTION

In view of the foregoing, it is an object of the present invention to provide a substance delivery device and method providing a sustained release without bringing patients discomfort by improving materials, structures and release process.

To achieve the above, the present invention discloses a substance delivery device comprising a dissolvable substrate, a plurality of dissolvable supporting structures, a plurality of degradable carriers and an adhesive. The dissolvable substrate configured to be attached to a tissue. The plurality of dissolvable supporting structures disposed on the dissolvable substrate, wherein each of the dissolvable supporting structures is a square and straight column, and each of the dissolvable supporting structures has a section whose area remains the same along a longitudinal axis of the dissolvable supporting structures. The plurality of degradable carriers disposed on the dissolvable supporting structures and encapsulating a plurality of first substances which are configured to be delivered into the tissue. The adhesive is disposed on each of the dissolvable supporting structures to stick with each of the corresponding degradable carriers. Wherein the dissolvable supporting structures are configured to be dissolved in the tissue after the degradable carriers and the dissolvable supporting structures are inserted into the tissue, so as to make the dissolvable substrate separate from the degradable carriers, and the degradable carriers are configured to swell and degrade to release the first substances into the tissue when the degradable carriers are left in the tissue. Wherein the dissolvable substrate and the dissolvable supporting structures are integrally formed, wherein the dissolvable substrate and the dissolvable supporting structures have the same material, and the material includes γ-poly-glutamic acid, hyaluronic acid, starch, gelatin, or their combinations.

In one embodiment of the present invention, a plurality of second substances are encapsulated in the dissolvable supporting structures and configured to be delivered into the tissue, and the second substances are the same as the first substances encapsulated in the degradable carriers.

In one embodiment of the present invention, a plurality of second substances are encapsulated in the dissolvable supporting structures and configured to be delivered into the tissue, and the second substances are different from the first substances encapsulated in the degradable carriers.

In one embodiment of the present invention, the degradable carriers include a material capable of melting after exposure to a radiation.

In one embodiment of the present invention, the degradable carriers include chitosan, chitin, silk, carboxymethyl cellulose, chondroitin, collagen, gelatin, polycaprolactone, poly(methyl vinyl ether-maleic anhydride), polyacrylic acid, 2-hydroxyethyl methacrylate, N,N-dimetyl acrylamide, maltose, hyaluronic acid, polylactic acid, polyglycolic acid, poly(lactic-co-glycolic acid), or their combinations.

In one embodiment of the present invention, the dissolvable substrate is configured to cover the tissue for less discomfort for user.

To achieve the above, the present invention discloses a substance delivery method applied with a substance delivery device. The substance delivery device comprises a dissolvable substrate, a plurality of dissolvable supporting structures, a plurality of degradable carriers and an adhesive. The dissolvable supporting structures are disposed on the dissolvable substrate, the dissolvable substrate. The dissolvable supporting structures are integrally formed with the same material. The degradable carriers are disposed on the dissolvable supporting structures and encapsulate a plurality of first substances which are configured to be delivered into the tissue. The adhesive is disposed on each of the dissolvable supporting structures to stick with each of the corresponding degradable carriers. Each of the dissolvable supporting structures is a square and straight column. Each of the dissolvable supporting structures has a section whose area remains the same along a longitudinal axis of the dissolvable supporting structures. The substance delivery method comprising the following steps: adhering the dissolvable substrate to a tissue so as to make the degradable carriers and the dissolvable supporting structures are inserted into the tissue; and after the degradable carriers and the dissolvable supporting structures are inserted into the tissue, dissolving the dissolvable supporting structures in the tissue so as to make the degradable carriers separate from the dissolvable substrate and swelling and degrading the degradable carriers to release the first substances into the tissue when the degradable carriers are left in the tissue, wherein the dissolvable supporting structures includes γ-poly-glutamic acid and hyaluronic acid.

In one embodiment of the present invention, the method further includes the following step: providing water or solution to the tissue or its surrounding.

In one embodiment of the present invention, the dissolvable supporting structures further include starch, gelatin, or their combinations.

In one embodiment of the present invention, a plurality of second substances are encapsulated in the dissolvable supporting structures, and the second substances are the same as the first substances encapsulated in the degradable carriers.

In one embodiment of the present invention, a plurality of second substances are encapsulated in the dissolvable supporting structures, and the second substances are different from the first substances encapsulated in the degradable carriers.

In one embodiment of the present invention, the degradable carriers include a material capable of melting after exposure to a radiation.

In one embodiment of the present invention, the degradable carriers include chitosan, chitin, silk, carboxymethyl cellulose, chondroitin, collagen, gelatin, polycaprolactone, poly(methyl vinyl ether-maleic anhydride), polyacrylic acid, 2-hydroxyethyl methacrylate, N,N-dimetyl acrylamide, maltose, hyaluronic acid, polylactic acid, polyglycolic acid, poly(lactic-co-glycolic acid), or their combinations.

In one embodiment of the present invention, the tissue includes skin, mucosa, cornea or sclera.

In one embodiment of the present invention, the dissolvable substrate is configured to cover the tissue for less discomfort for user.

To achieve the above, the present invention discloses a substance delivery device comprising a dissolvable substrate, a plurality of dissolvable supporting structures, a plurality of degradable carriers and an adhesive. The dissolvable substrate configured to be attached to a tissue. The plurality of dissolvable supporting structures disposed on the dissolvable substrate, wherein each of the dissolvable supporting structures is a square and straight column, each of the dissolvable supporting structures has a section whose area remains the same along a longitudinal axis of the dissolvable supporting structures, a height of the dissolvable supporting structures ranges from 600 μm to 900 μm and a width of the dissolvable supporting structures ranges from 200 μm to 400 μm. The plurality of degradable carriers disposed on the dissolvable supporting structures and encapsulating a plurality of first substances which are configured to be delivered into the tissue. The adhesive is disposed on each of the dissolvable supporting structures to stick with each of the corresponding degradable carriers. Wherein a height of the degradable carriers ranges from 400 μm to 800 μm and a width of one end of the degradable carriers connected to the dissolvable supporting structures ranges from 200 μm to 400 μm. Wherein the dissolvable supporting structures are configured to be dissolved in the tissue after the degradable carriers and the dissolvable supporting structures are inserted into the tissue, so as to make the dissolvable substrate separate from the degradable carriers, and the degradable carriers are configured to swell and degrade to release the first substances into the tissue when the degradable carriers are left in the tissue. Wherein the dissolvable substrate and the dissolvable supporting structures are integrally formed, wherein the dissolvable substrate and the dissolvable supporting structures have the same material, and the material includes γ-poly-glutamic acid, hyaluronic acid, starch, gelatin, or their combinations.

In one embodiment of the present invention, the dissolvable substrate is configured to cover the tissue for less discomfort for user.

As mentioned above, the substance delivery device of the present invention applies a combination of dissolvable supporting structures and carriers to make a delivery system capable of delivering substances through tissues, especially through skin or mucosa. Meanwhile, the present invention also provides a substance delivery device which is characterized by its novel releasing steps to release substances in a sustained manner. Furthermore, the dissolvable supporting structure of the substance delivery device of the present invention is able to be dissolved by the body fluid and/or interstitial fluid in the skin. The carriers are then left in the inserted skin and swell and degrade to gradually release the drug in a sustained manner. Accordingly, the effectiveness of the substances may last longer. More importantly, compared to the traditional patches which are necessary to attach on the skin for quite a long time to maintain its effectiveness, the substance delivery device of the present invention and the method thereof are not necessary to stick the substrate on the skin during the releasing of the drug, and it significantly decreases the contacting time to the skin. Therefore, the possibility to induce symptoms of allergy, such as itching and skin rashness, is diminished and patients' discomfort is also reduced.

BRIEF DESCRIPTION OF THE DRAWINGS

The present invention will become more fully understood from the subsequent detailed description and accompanying drawings, which are given by way of illustration only, and thus are not limitative of the present invention and wherein:

FIG. 17A shows the results of microneedles with γ-poly-glutamic acid supporting structures (γ-PGA); FIG. 17B shows the results of microneedles with hyaluronic acid supporting structures (HA).

DETAILED DESCRIPTION OF THE INVENTION

The present invention will be apparent from the following detailed description, which proceeds with reference to the accompanying drawings, wherein the same references relate to the same elements.

Figure 1:
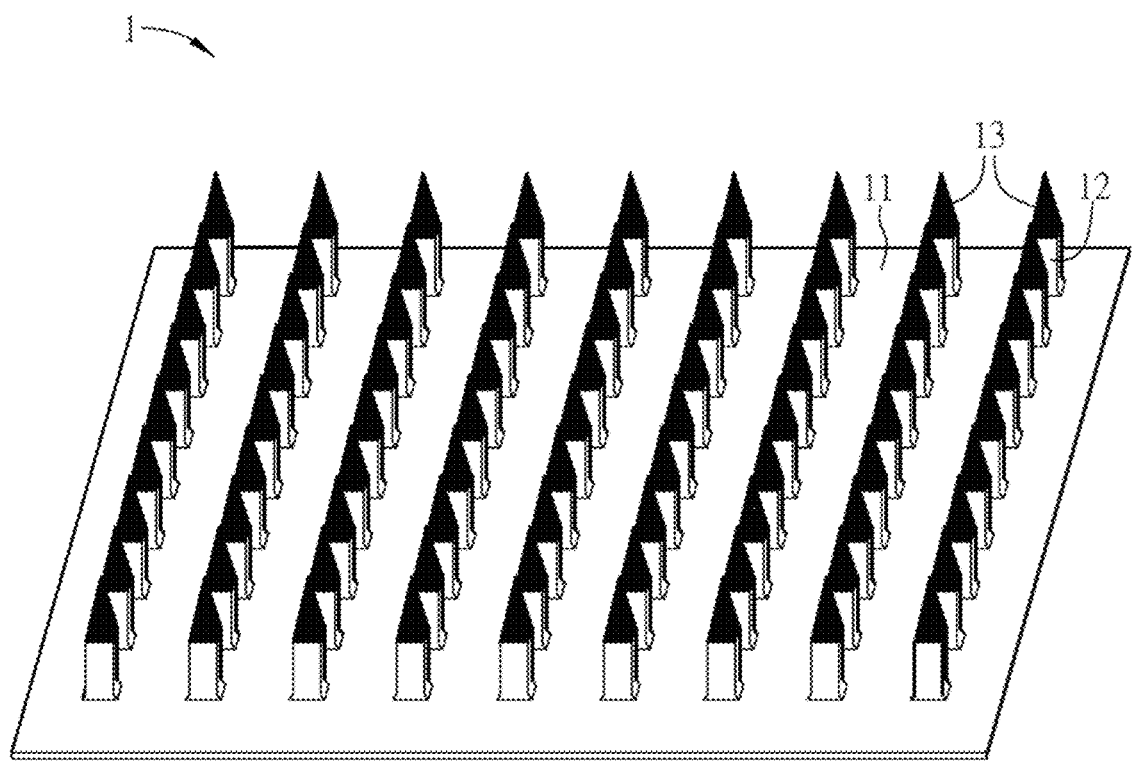
FIG. 1 is a schematic view of a substance delivery device according to preferred embodiment of the present invention.
Figure 2:
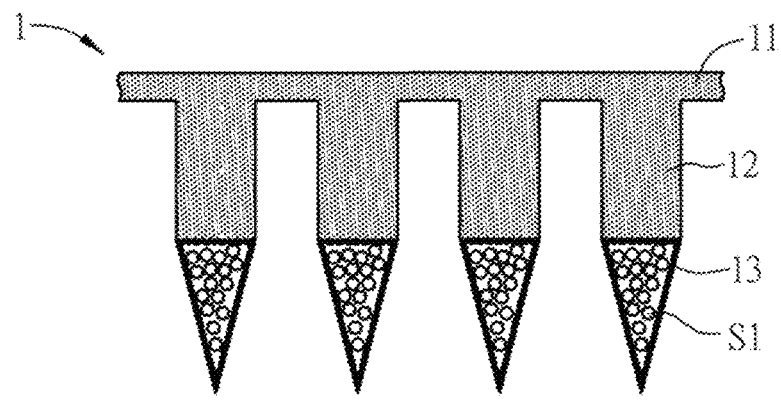
FIG. 2 is a partially schematic view of a substance delivery device of FIG. 1.

FIG. 1 is a schematic view of a substance delivery device according to preferred embodiment of the present invention. FIG. 2 is a partially schematic view of a substance delivery device of FIG. 1. With reference to FIG. 1, in this embodiment, substance delivery device 1 includes a substrate 11, a plurality of dissolvable supporting structures, and a plurality of carriers. In detail, the dissolvable supporting structures 12 are disposed on the substrate. The carriers 13 are disposed on the dissolvable supporting structures 12. The carriers 13 encapsulate a plurality of substances S1. In this embodiment, the substances S1 is substantially single chemical component and structure; however, this description is not meant to be construed in a limiting sense. Substances S1 may be a mixture formed with different kinds of substance. It depends on the use of the substance delivery device 1.

In this embodiment, the word "individual" used here is collectively referred to an organism mainly including mammals, such as mouse, human, rabbit, cattle, sheep, pigs, monkeys, dogs or cats, preferably human. In this embodiment, tissue is preferably human skin, mucosa, cornea tissue or sclera tissue. Skin includes all the tissues included in the skin organ, like epithelial tissue; mucosa widely includes epithelial tissue or connective tissue which is visible on human appearance and is able to secrete mucus, such as oral cavity or vagina.

With reference to FIG. 1 and FIG. 2, substrate 11 is mainly formed with materials obtaining high mechanical strength, such as polyvinylpyrrolidone, polyvinyl alcohol, γ-poly-glutamic acid, hyaluronic acid, starch, gelatin, or their combinations.

A plurality of rectangular columnar dissolvable supporting structures 12 are disposed on the substrate 11 individually. In practical use, the dissolvable supporting structures 12 are not limited to rectangular columnar shape, which can be adjusted to meet the structure and size of carriers 13. In detail, the dissolvable supporting structures 12 of the present invention can be dissolved in the tissue they contacted, such as, but not limited to dissolve in tissue fluid or other body fluid. Thus, the dissolvable supporting structures 12 can be used as a bridge of substrate 11 and the carriers 13. That is, the substrate 11 and the separation time between the substrate 11 and the carriers 13 can be controlled by the selected materials and the structure design of dissolvable supporting structures 12. The dissolvable supporting structures 12 include polyvinylpyrrolidone, polyvinyl alcohol, γ-poly-glutamic acid, hyaluronic acid, starch, gelatin, or their combinations.

In this embodiment, the substrate 11 and the dissolvable supporting structures 12 are both composition of polyvinylpyrrolidone and polyvinyl alcohol. And the substrate 11 and the dissolvable supporting structures 12 are integrally formed.

In detail, before forming the substrate 11 and the dissolvable supporting structures 12, Polydimethylsiloxane solution should be prepared first. Polydimethylsiloxane solution is prepared by mixing agent A (PDMS substrate) with agent B (curing agent) in a ratio of 10:1 and then incubating in a shaking bath. Bubbles in the solution are removed, and the solution is then poured into a mother mold. After the bubble is floated out, the mother mold mentioned above is incubated in a 90□ oven for curing. After incubating for approximately 30 minutes, the molds of substrate 11 and dissolvable supporting structures 12 are well prepared. However, the detailed manufacturing process of mold is well-understood by the person having ordinary skill in the art, and are not repeated here.

Then, the materials for manufacturing the substrate 11 and dissolvable supporting structures 12 are prepared. First of all, polyvinylpyrrolidone and polyvinyl alcohol are mixed with ratio 1:1. In detail, polyvinylpyrrolidone, polyvinyl alcohol and deionized water are mixed with ratio 1:1:2. And then, the mixed solution is placed on the mold and centrifuged for 30 minutes (5100 rpm, 30□) to fill the mold cavities. After the centrifugation, the mold is dried at room temperature for 1 day. Completing all the process steps above, the integrally formed substrate 11 and dissolvable supporting structures 12 is obtained.

Figure 3:
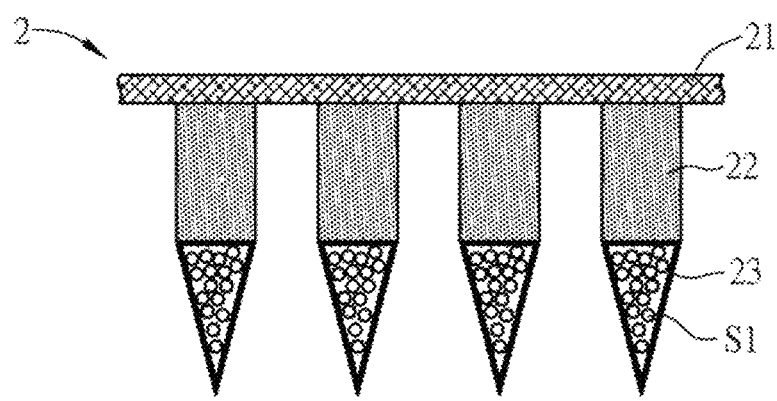
FIG. 3 is a partially schematic view of a substance delivery device with different substrate according to another embodiment of the present invention.

Particularly, in other embodiments, the substrate and dissolvable supporting structures may be formed individually with different molds. With reference to FIG. 3, the substrate 21 of substance delivery device 2 may be non-dissolvable in order to be easily removed after the dissolvable supporting structures 22 are dissolved. However, the detailed application manner of substance delivery device 2 is substantially the same as substance delivery device 1, and is not repeated here.

With reference to FIG. 1 and FIG. 2, carriers 13 is the structure firstly contacted with the tissue of individuals of substance delivery device 1. Therefore, for entering into tissue, carriers 13 of this embodiment are in a square pyramidal shape, for example. In other practical use, the carrier 13 may be in a microneedle shape, cone shape or any shape which can easily penetrate skin, and the present invention is not limited to these aforementioned examples.

In this embodiment, the material of the carriers 13 maybe chitosan, chitin, silk, carboxymethyl cellulose, chondroitin, collagen, gelatin, polycaprolactone, poly(methyl vinyl ether-maleic anhydride), polyacrylic acid, 2-hydroxyethyl methacrylate, N,N-dimetyl acrylamide, maltose, hyaluronic acid, polylactic acid, polyglycolic acid, poly(lactic-co-glycolic acid), or their combinations.

In this embodiment, the size of the dissolvable supporting structures 12 and the carriers 13 may be limited in a range in order to prevent the carriers 13 from over-penetrating which may cause pain or hurt patients. The height of dissolvable supporting structures 12 may ranges from 200 μm~1000 μm and preferably ranges from 600 μm~900 μm. The width of the end of the dissolvable supporting structures 12 connected to the carriers 13 may ranges from 100 μm~500 μm and preferably ranges from 200 μm~400 μm. The height of the carriers 13 may ranges from 200 μm~1000 μm and preferably ranges from 400 μm~800 μm. The width of the end of carriers 13 connected to the dissolvable supporting structures 12 may ranges from 100 μm~500 μm and preferably ranges from 200 μm~400 μm. With the configurations mentioned above, the carriers 13 are able to penetrate the stratum corneum and reach the dermal layer of the skin. The penetration depth may ranges from 200 μm~1000 μm and preferably ranges from 250 μm~1,000 μm.

Formation of the carriers 13 also needs PDMS mold preparation. However, the same manufacturing process of mold has been described above, and is not repeated here. When the mold is formed, the chitosan hydrogel loaded with substances S1 is then used for centrifugal mold filling. Similarly, the encapsulation process of substance S1 and the preparation method of chitosan hydrogel is well-understood by the person having ordinary skill in the art or referenced by the following experiments, and is not repeated here.

The substances delivered by the substance delivery device 1 of the present invention are not limited. Preferably, the substances may include a drug or biological active substances. The biological active substances include but not limited to enzyme, antibody, hormone, transcription factor or translation factor. Any other substances which are able to activate physiological or biochemical reaction may also be delivered by the substance delivery device 1 of the present invention.

After formation of substrate 11, dissolvable supporting structures 12 and carriers 13, one end of the dissolvable supporting structures 12 then dips into polyvinylpyrrolidone/polyvinyl alcohol solution and make a small amount of solution mounted on the end. The dissolvable supporting structures 12 are aligned with the cavities of the mold containing carriers 13 and then pressed to the mold to make the dissolvable supporting structures 12 stick with the carriers 13. After drying, the substance delivery device 1 is obtained. The number of the carriers 13 and the dissolvable supporting structures 12 comprised in one substance delivery device 1 may be varied with the amount of the substance Si needed to be delivered and other conditions in the practical use, to administrate an effective dosage of a drug. However, it is not a limitation of the present invention.

As mentioned above, the dissolvable supporting structures 12 are dissolvable. Hence, when the substrate 11 attaches to the tissue (not shown in Figure), the dissolvable supporting structures 12 can be dissolved by the tissue fluid in the tissue. The carriers 13 are separated from the substrate 11 accordingly, and are left in the tissue. Furthermore, the carriers 13 are able to swell in the skin of the individual and degrade naturally to release the substances S1 into the tissue. In practical use, water or solution may be applied to the tissue or its surrounding to accelerate the separation of carriers 13 and substrate 11. In addition, a traditional sustained-release microneedle patch is necessary to be attached on the skin of the patient for several days or even weeks to release the drug or biological active substances from degraded carriers, which may bring user discomfort and inconvenience. However, when the substance delivery device 1 is applied on an individual, the carriers 13 can be separated from the substrate 11 and left in the tissue to exert its sustained effect as soon as the dissolvable supporting structures 12 are dissolved. The substrate 11 is therefore not necessary to attach on the skin of the individual during the substance S1 releasing from the carrier 13. Accordingly, the substance delivery device 1 not only improves the application convenience, but mitigates or even prevents the discomfort for user. The release time of the substances S1 in tissue is based on the polymer materials of the carriers 13 and the molecular weight of the substances S1.

Chitosan carriers can act as an adjuvant to promote Th1 and Th2 immune responses. Compared to traditional oral or needle administration, the substance delivery device 1 generates a greater immune response because it uses chitosan as the material for carriers 13 and the vaccine is administrated by TDD. Preferably, in one of the embodiment of the present invention, the substance delivery device 1 is act as a formulation of vaccine. Through the sustained release property, the substance delivery device 1 is able to boost the immune response targeted to the specific antigen, and the total dosage and the administration times of the vaccine can be decreased.

In addition, the substrate 11 of the present embodiment may be also dissolvable as the dissolvable supporting structures 12 is. Hence, the substrate 11 and the dissolvable supporting structures 12 will be dissolved when contacting tissue fluid, body fluid, water, or solutions. This prevents medical personnel and users from recycling the substrate 11. In detail, because the materials of substrate 11 and the dissolvable supporting structures 12 are bio-compatible substances which are not harmful to the individual; accordingly, no medical waste problems need to be concerned.

Figure 4:
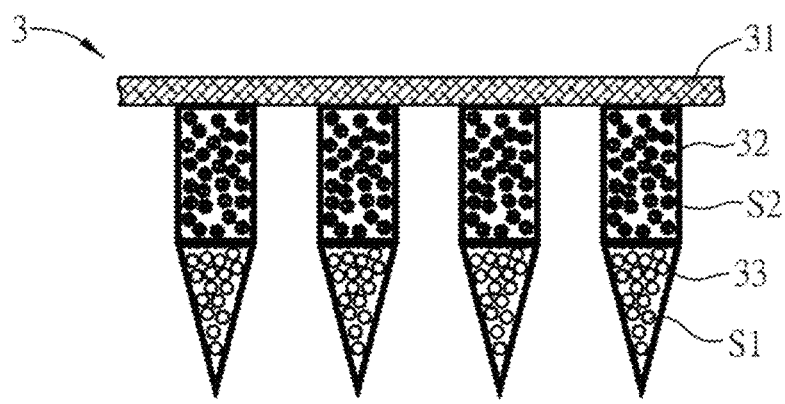
FIG. 4 shows partially schematic view of a substance delivery device according to another embodiment of the present invention.

Furthermore, the substance delivery device of the present embodiment is able to provide quick release and sustained release for substances. FIG. 4 shows partially schematic view of a substance delivery device according to another embodiment of the present invention. With reference to FIG. 4, in this embodiment, substances S2 and substances S1 is encapsulated in the dissolvable supporting structures 32 and the carriers 33, respectively. The substances S2 encapsulated in the dissolvable supporting structures 32 and the substance S1 encapsulated in the carriers are different substances.

Through the configuration that the substances S2 and the substance S1 are encapsulated separately, the dissolvable supporting structures 32 is able to release the substances S2 rapidly, and the carriers 33 is able to provide the substances Si in a sustained-release manner due to its materials which costs more time to degrade. In other words, different substances are encapsulated in the dissolvable supporting structure 32 and carriers 33, respectively, which provides more than one category of substances in a single attachment. For example, when the user is a diabetic patient, substance delivery device 3 encapsulating both insulin (substances S2) and influenza vaccine (substances S1) may be suitable for such patients. Thus, the patients may accept rapid release of insulin and alleviate the symptoms of diabetes; at the same time, patients can get immunity through the sustained-release of influenza vaccines without another administration. The discomfort caused by multiple administrations of a vaccine is therefore reduced and the possibility of infection is also decreased.

In addition, the present invention is not limited to the embodiments described above. In addition, substance S1 and substances S2 may also be the same substances to apparently increase the total encapsulated amount of drugs and biological active substances. Such configuration may achieve both quick release and sustained release effect.

Furthermore, in other embodiments, in order to more precisely control the time of the substances released from the carriers, the carriers may further encapsulate indocyanine green or metal nanoparticles and thus form a material which is capable of melting after exposure to a radiation. The word "radiation" used here is collectively referred to electromagnetic radiation which preferably including near-infrared light, infrared light, or microwave. Such material can be polycaprolactone (PCL), gelatin, methylcellulose or polyethylene oxide (PEO).The metal nanoparticles may be gold nanoparticles, gold nanorods, gold and silver nanoballs, or germanium nanoparticles. Preferably, the nanoparticles can also be a single-walled carbon nanotubes, or lanthanum hexaboride nanoparticles. In detail, when radiation is applied to the carriers, the indocyanine green or metal nanoparticles will absorb the radiation and convert the radiation into heat. The heat will then melt the material of the carriers. As a result, the carriers can be melt after exposure to a radiation, and the substances (drugs or biological active substances) will be released into the tissue. Therefore, the substances carried in this application are preferably with good heat stability, such as DNA, polysaccharides, thermal-stable vaccine, thennal-stable enzyme or synthetic drugs. However, this description is not meant to be construed in a limiting sense.

Figure 5:
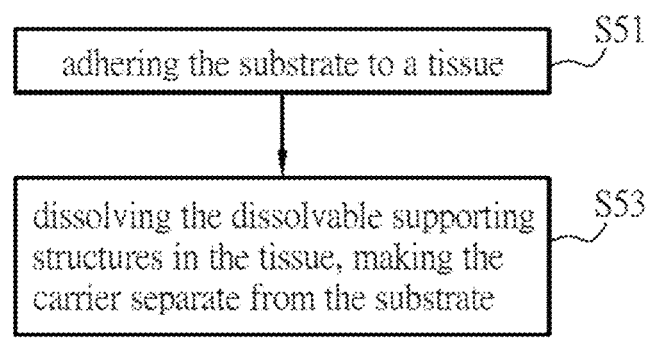
FIG. 5 is a flow chart showing the steps of the substance delivery method according to another embodiment of the present invention.

FIG. 5 is a flow chart showing the steps of the substance delivery method according to another embodiment of the present invention. With reference to FIG. 5, in this embodiment, substance delivery method is applied with the substance delivery device in the foregoing examples. The substance delivery method includes the following steps: adhering the substrate to a tissue (S51); and dissolving the dissolvable supporting structures in the tissue, making the carrier separate from the substrate (S53). However, the structure and the implementation details have been described above, and are not repeated here.

Figure 6A:
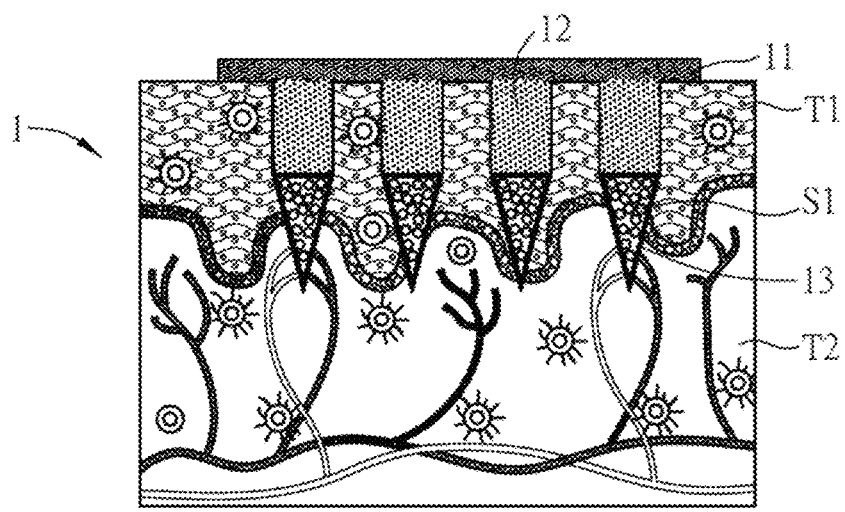
FIG. 6A~6C is an application flow chart of substance delivery method according to FIG. 5.
Figure 6B:
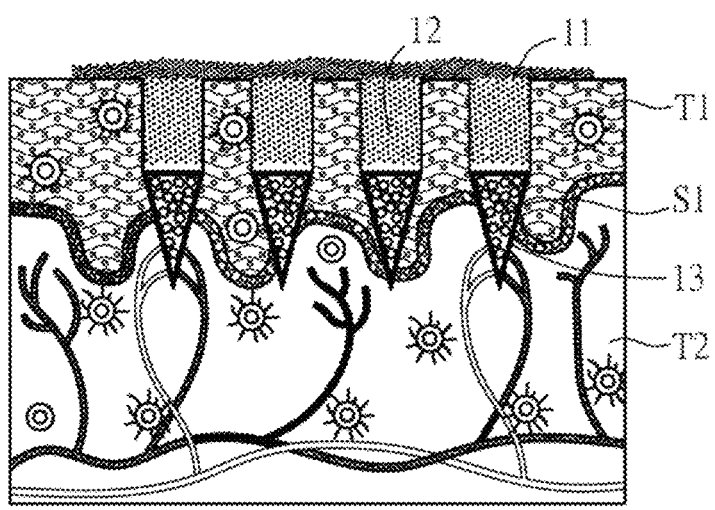
Figure 6C:
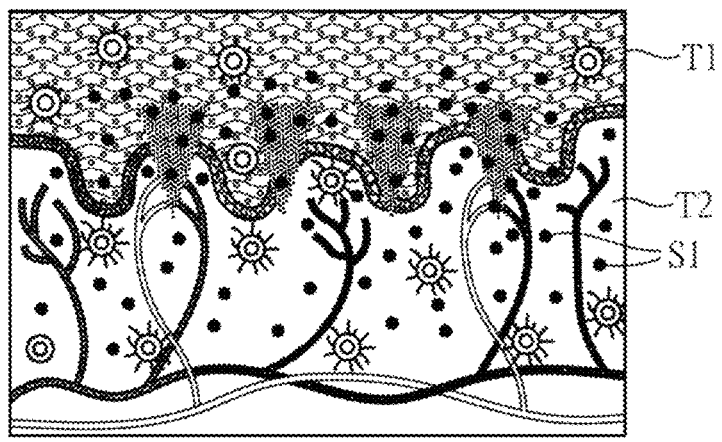

FIG. 6A~6C is an application flow chart of substance delivery method according to FIG. 5. With reference to FIGS. 5~6C and the structure of the substance delivery device showed in the embodiments mentioned above, in step S51, the substance delivery device 1 attaches to the tissue by the end of the carriers 13 (shown in FIG. 6A). This embodiment takes skin as an example. The skin includes epidermis T1, dermis T2 and subcutaneous tissue (not shown in figure) from outer layer to the inner side. Most drugs and biological active substances need to infiltrate through the stratum corneum of the epidermis T1 to achieve efficient transdermal delivery. Therefore, the carries 13 and the dissolvable supporting structures 12 of the present embodiment have to be at least inserted into the epidermis T1. After the substance delivery device 1 is attached onto the tissue, in steps S53, the tissue fluid, water or other solutions in the tissue is able to dissolve the dissolvable supporting structures 12, further separating the carriers 13 from the substance delivery device 1 (as shown in FIG. 6B). In this moment, a plurality of the carriers 13 are left in the tissue. The substances S1 are therefore released in a slow but sustained manner, through the gradual swelling and degradation of the carriers 13.

In detail, the substance delivery device of the present invention further includes the step of providing water or solution to the tissue or its surrounding, which is not limited to be done before or after the step S51, and the type of solution added is also not limited. The added solution is chosen based on the materials of the substrate and dissolvable supporting structures.

The following and accompanying figures take a number of experiments for examples to describe the manufacturing method of the substance delivery device and the practical applying method and the effect of the implantation of the substance delivery device in accordance with the embodiments of the present invention.

Experiment 1

Manufacture of the Substance Delivery Device

Materials

Sodium hyaluronate (HA) with molecular weight (MW) of 7 kDa and 250 kDa was purchased from Bloomage Freda Biopharm (Jinan, China) and Kewpie (Tokyo, Japan), respectively. Chitosan (viscosity=22 mPa·s for 3.2% in 1% acetic acid at 20° C., and degree of deacetylation=91.2%,), γ-poly-glutamic acid (γ-PGA; $Na^+$ form, MW approximately 1000 kDa), and PVA (MW=6000) were obtained from Koyo Chemical (Osaka, Japan), Vedan Enterprise Corp (Taichung, Taiwan), and Polysciences (Warrington, Pa., USA). Rhodamine 6G (MW=470), fluorescein 5(6)-isothiocyanate (FITC; MW=389), and PVP (MW=10000) were purchased from Sigma-Aldrich (St. Louis, Mo., USA).

Manufacture of Molds

Figure 7A:
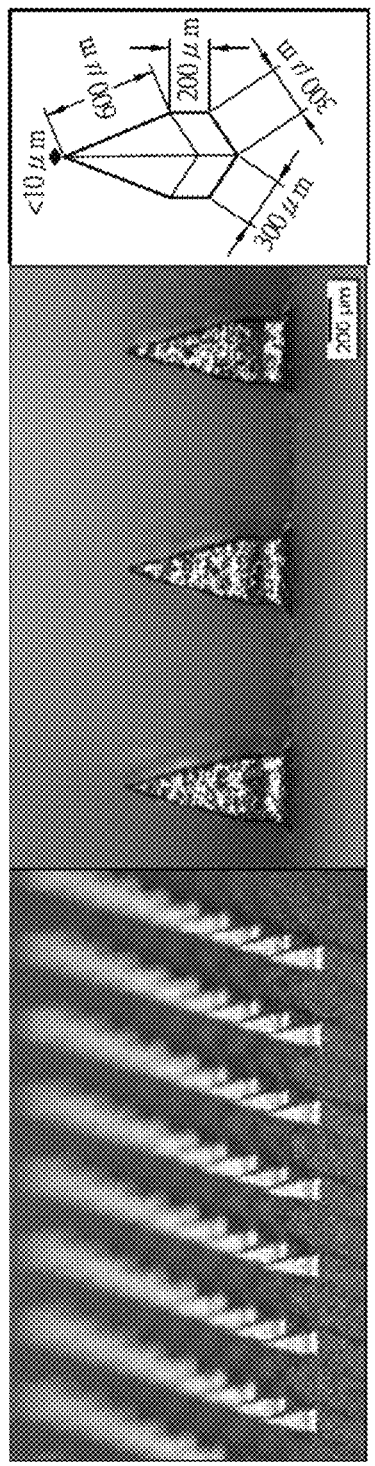
FIG. 7A and FIG. 7B are photos of the mother mold of the substance delivery device according to preferred embodiment of the present invention.
Figure 7B:
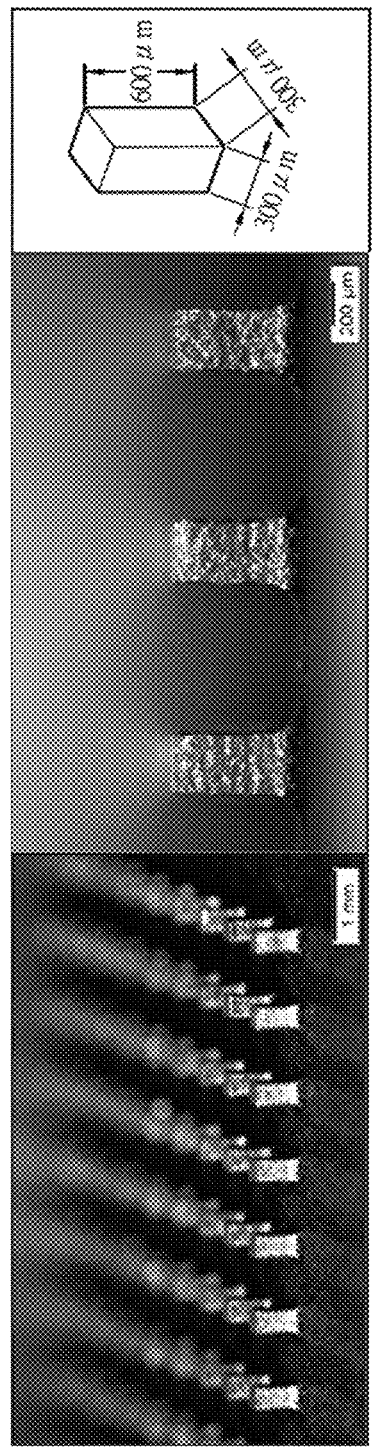

Polydimethylsiloxane solution is prepared by mixing agent A with agent B in a ratio of 10:1 and then incubating in a shaking bath. The bubble in the solution is removed, and stainless steel mother molds of microneedles (as shown in FIG. 7A) and supporting structure (FIG. 7B) were immersed in the solution. The size of the mother mold of microneedles is: the bottom size 300 μm×300 μm, height of needle 600 μm, height of base 200 μm, total height 800 μm, in a 9×9 array; and the size of the mother mold of supporting structure is: the bottom size 300 μm×300 μm, height 600 μm, in a 9×9 array. PDMS completely covers the two mother molds. After the bubble is floated out, both of the mother molds mentioned above are incubated in a 90° C. oven for 30 minutes for curing. Microscaled molds for microneedle and supporting structure are formed.

Manufacture of Dissolvable Supporting Structure 5 g of PVP, 5 g of PVA and 10 ml of deionized water (PVP:PVA:DI water=1:1:2) are mixed for preparing PVP/PVA solution; 3 g of γ-PGA is dissolved in 2 ml of deionized water for making γ-PGA solution; 12 g of 7 kDa HA, 6 g of 250 kDa HA, and 82 ml of deionized water are mixed for preparing HA solution. 0.5 mg of rhodamine 6G is added to the prepared polymer solution and 0.5 g of of the resulting solution is placed on the mold of supporting structure and centrifuged for 30 minutes (5100 rpm, 30° C.). After the centrifugation, the mold is dried at room temperature for 1 day. At last, the supporting structure array (including the dissolvable supporting structure and the substrate of the present invention) is peeled from the mold.

Manufacture of Carrier 180 mg of chitosan hydrogel (13% (w/w)) is placed on the mold of microneedles. and centrifuged for 2 hours (5100 rpm, 30° C.). After the centrifugation, PVP/PVA solution (about 0.1 g) is covered on the hydrogel in order to apply pressure on the chitosan hydrogel. The mold is dried at room temperature for 1 day. The excess polymer on the mold of microneedle is cut off by the blade of a frozen-section apparatus, and the chitosan microneedle (i.e. the carriers of the present invention) remains in the mold.

Formation of Substance Delivery Device

Figure 8A:
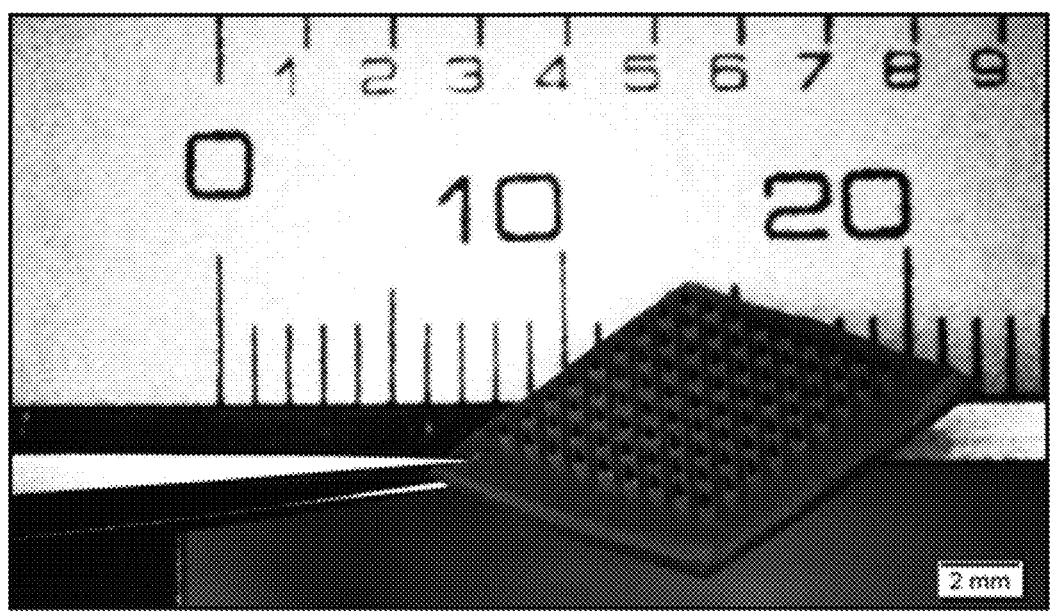
FIG. 8A shows optical microscope image of the microneedle patch array.
Figure 8B:
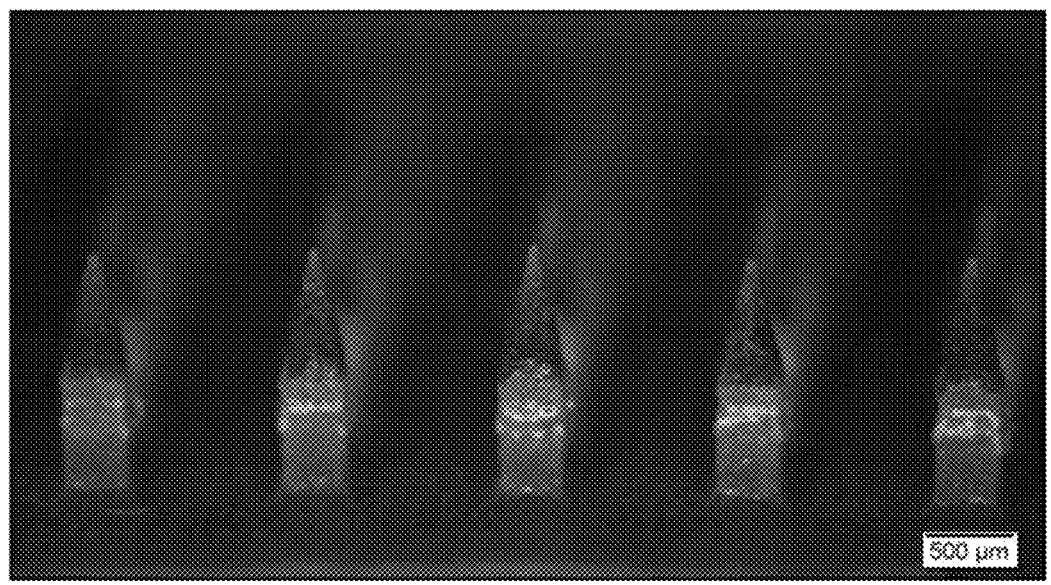
FIG. 8B shows 5 times magnifying schematic view of FIG. 8A.

The tips of the supporting structure array are dipped with a small amount of PVP/PVA solution (50% (w/w)), and then the columnar parts of the supporting structure array are aligned with the cavities of the mold including chitosan microneedles. The supporting structure array is then gently pressed down to the mold including chitosan microneedles, to make supporting structures stick with chitosan microneedles. After drying for 20 minutes in 37° C. oven, the microneedle patch is formed (i.e. the substance delivery device 1 shown in FIG. 8A and FIG. 8B). FIG. 8A represents a light microscopic image of the microneedle patch array, and FIG. 8B shows a 5-times magnifying image of FIG. 8A.

Experiment 2

In Vitro Skin-Insertion

Substance delivery device including dissolvable substrate, dissolvable supporting structure, and carriers is prepared. To assess whether the chitosan microneedle has sufficient penetrating ability or not, porcine cadaver skin is used for in vitro insertion test.

Particularly, a microneedle patch applicator is used herein to assist and prevent an incomplete insertion caused by an uneven force. The structure of the applicator includes a spring and column. The spring is able to push the column and make the microneedle patch located at the front end of the column penetrate into the skin. The penetrating force can be adjusted by adjusting the spring. This device is able to assist users to insert the microneedles into skin within 3 seconds to achieve stable complete insertion.

Before insertion process, hairs of porcine cadaver skin are removed. After the treatment, the microneedle patch is inserted into porcine cadaver skin by using a homemade applicator and conducting the puncture experiment. The applicator has a water injector which provides water for an adequate amount to assist the dissolvable supporting structure to dissolve after the microneedle patch is inserted. The application time is 5-10 minutes (approximately 10 N/patch). After the insertion process is done, marks on the skin caused by the microneedles inserting into skin are observed by optical microscopy for histological analysis. The result of porcine cadaver skin after insertion of the microneedle patch is shown in FIGS. 9A~9C.

Figure 9A:
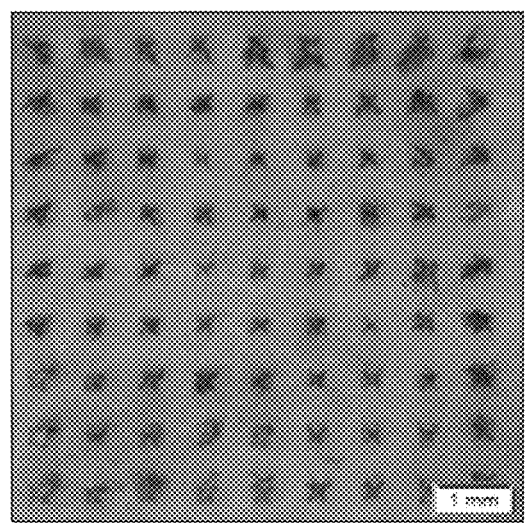
FIG. 9A shows image of porcine cadaver skin after microneedle insertion and staining with blue tissue marking dye.
Figure 9B:
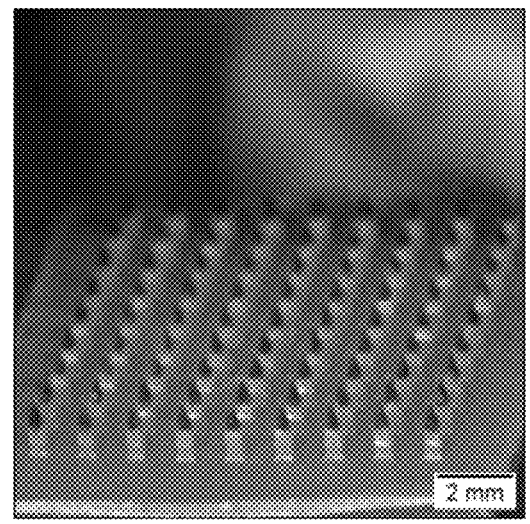
FIG. 9B shows image of microneedle patch before skin insertion.
Figure 9C:
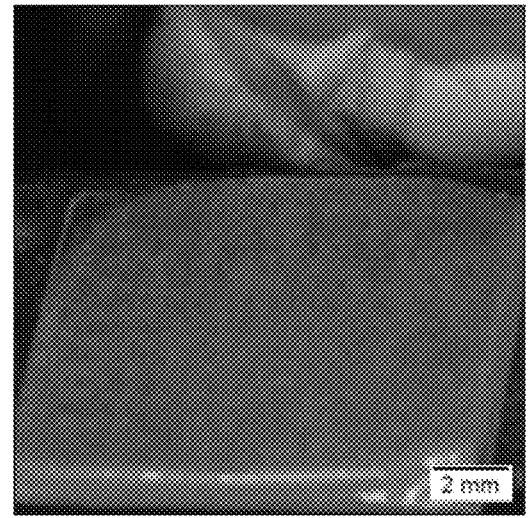
FIG. 9C shows image of patch after skin insertion.

FIG. 9A shows staining image of porcine cadaver skin after microneedle insertion by applicator. FIG. 9B shows image of microneedle patch before skin insertion. FIG. 9C shows image of microneedle patch after skin insertion. With reference to FIGS. 9A~9C, in the insertion process, the applicator is able to provide force in vertical downward direction and concentrate the force on the chitosan microneedles to apply pressure on the skin. Thus, the chitosan microneedles penetrate stratum corneum and create micro-channels. Meanwhile, the supporting structure is dissolved by water provided by the water injector of the applicator. Then, the chitosan microneedles can be left and embedded in porcine cadaver skin. porcine cadaver skin is then stained with tissue marking dye. The marks caused by the insertion of the microneedle array is apparent in FIG. 9A. Furthermore, before insertion, the structure of microneedle array is intact. After insertion, no chitosan microneedles are left on the patch, as shown in FIG. 9C.

Experiment 3

In Vivo Insertion and Wound Healing

The in vivo skin insertion ability of microneedles and the skin resealing after microneedle insertion were evaluated in three individuals, including ICR mice, Sprague-Dawley rat (SD rat) and LYD hog. Before insertion process, the hair of the pig skin is removed. The microneedle patch is fixed on the applicator and then inserted into the skin for 3 minutes. After the insertion process is done, the array marks caused by the microneedles inserting into skin is observed by optical microscopy. The result is shown in FIG. 10A~10C.

Figure 10C:
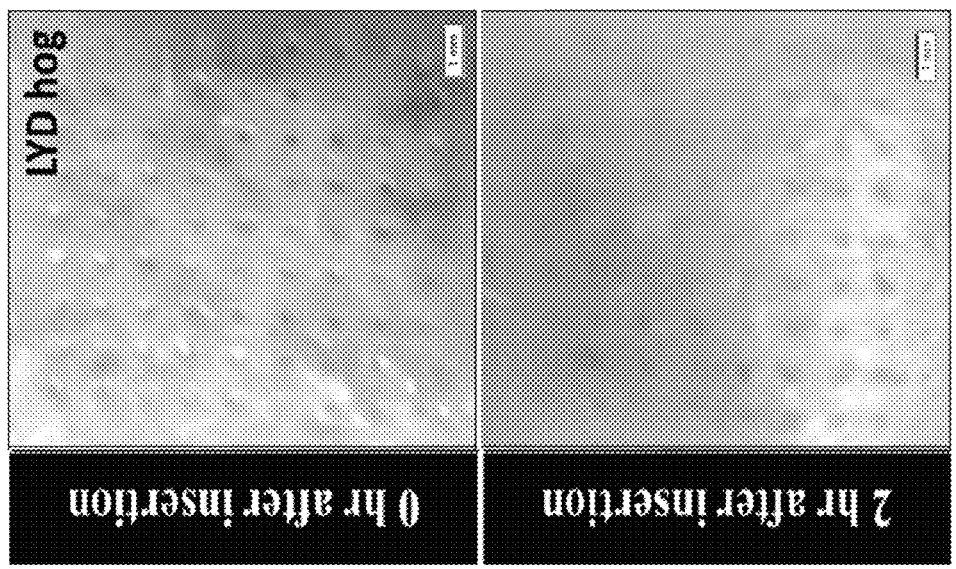
FIG. 10C shows skin image of LYD hog at 0 (top) and 2 h (bottom) after puncture by microneedles.
Figure 10B:
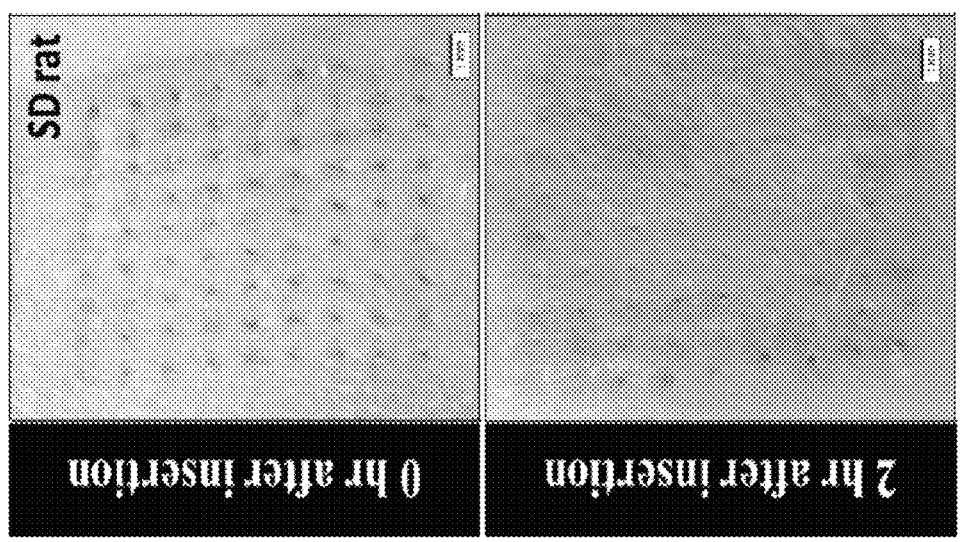
FIG. 10B shows images of dorsal skin of SD rat at 0 (top) and 2 h (bottom) after puncture by microneedles.
Figure 10A:
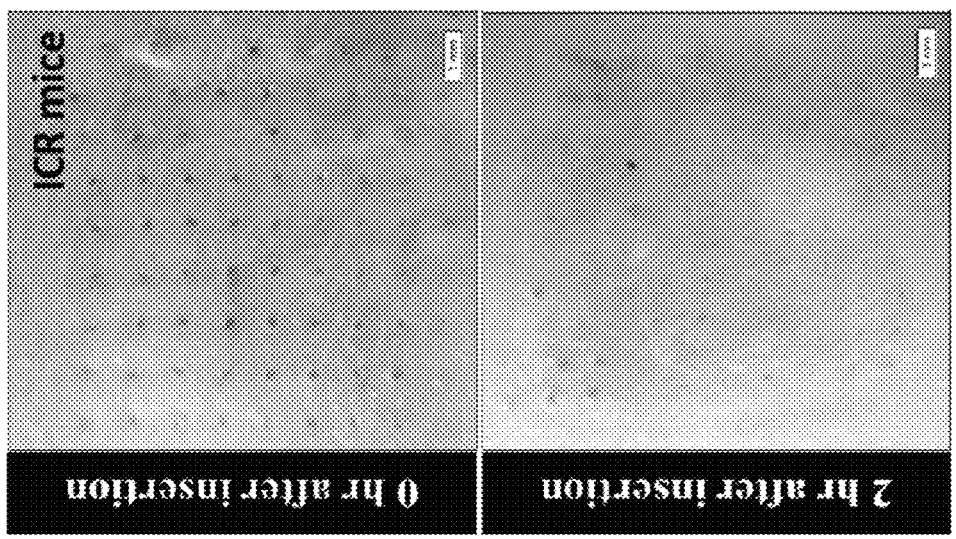
FIG. 10A shows images of dorsal skin of ICR mice at 0 (top) and 2 h (bottom) after puncture by microneedles.

FIG. 10A shows images of the skin of ICR mice after insertion of microneedles, FIG. 10B shows image of the skin of Sprague-Dawley rat after insertion of microneedles by applying an applicator, and FIG. 10C shows image of the skin of LYD hog after insertion of microneedles by applying an applicator. With reference to FIG. 10A~10C, the upper images represent the results observed immediately after the insertion, and the lower images represent the result observed after two hours from the insertion. As shown in FIG. 10A~10C, the marks of the microneedle array are quite clear and distinct immediately after the insertion. After two hours from the insertion, the microchannels caused by the insertion had almost resealed.

Stratum corneum acts as a protective layer of the skin to prevent underlying tissue from dehydration. When the stratum corneum is inserted by the chitosan microneedles and microchannels are formed therein, the trans-epidermal water loss (TEWL) will increase because the water in the skin may evaporate through the microchannels. However, skin heals automatically and gradually after wounded. Therefore, by estimating the trans-epidermal water loss, the degree of wound healing may be assessed. In the group of SD rat, the TEWLs of penetrated areas and areas without penetrating are measured side-by-side via contacting a probe of a vapor meter to the skin at 0, 10, 30, 60, 120, 180, 240, 300 and 360 minutes after the insertion of the microneedles. The result is shown as FIG. 11.

Figure 11:
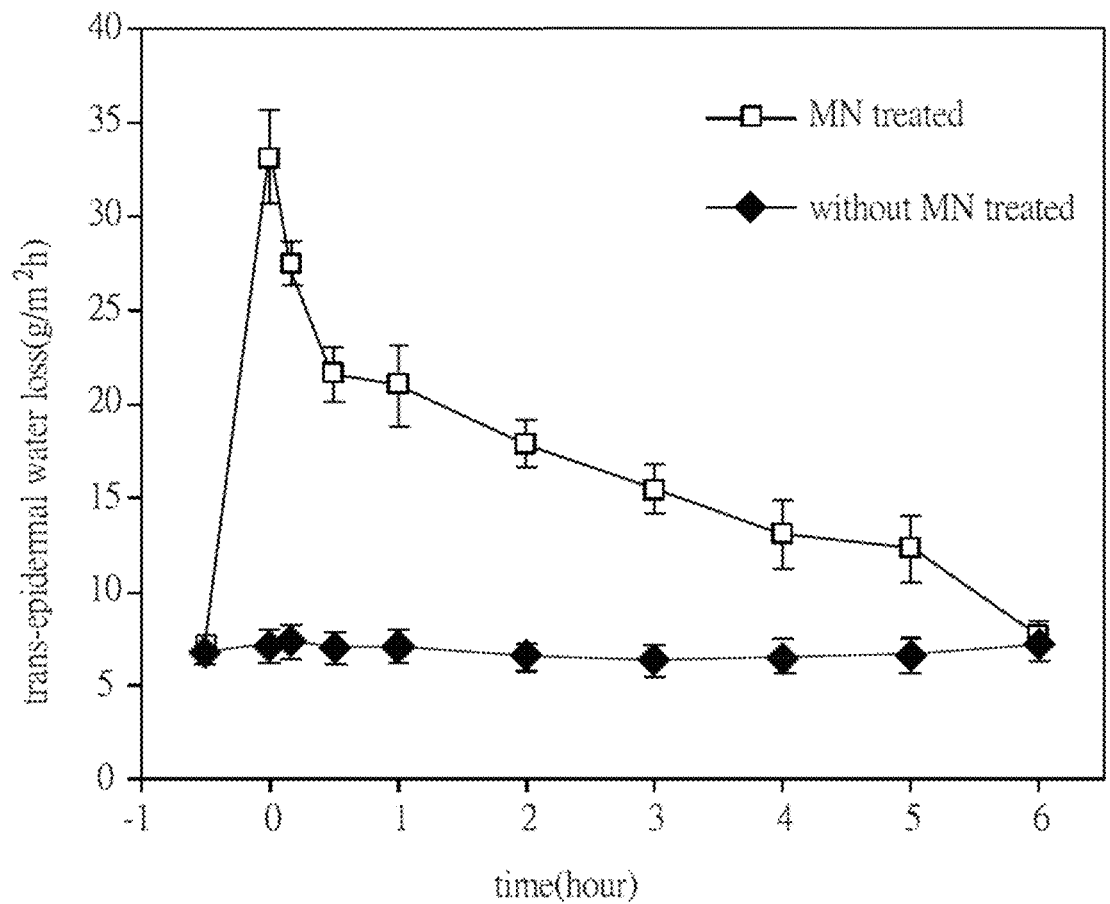
FIG. 11 shows the trans-epidermal water loss values of SD rat's skin after microneedle puncture.

FIG. 11 shows TEWL values of SD rat's skin after microneedle insertion. With reference to FIG. 11, after insertion, the trans-epidermal water loss of penetrated area increases significantly. As shown in FIG. 11, the penetrated areas are gradually healed with time increasing. After six hours of the penetration, the trans-epidermal water loss is recovered to the same value as high as the areas without penetration. This proves a rapid healing of microneedle-created wound, which will prevent damaged skin from infection.

Experiment 4

Degradation of Chitosan Microneedle 4-week-old Sprague-Dawley rats are anesthetized and shaved. Rats are sacrificed on the first (day 0), $7^{th}$, $14^{th}$, $21^{st}$ and $28^{th}$-day after microneedle insertion, respectively. The skin where the microneedles are inserted is collected with size 1 cm×1 cm, and the skin is then embedded for frozen sections to observe the result of degradation of chitosan microneedles in the skin. The degradation behavior of the chitosan microneedles in the rat skin is shown as FIG. 12.

Figure 12:
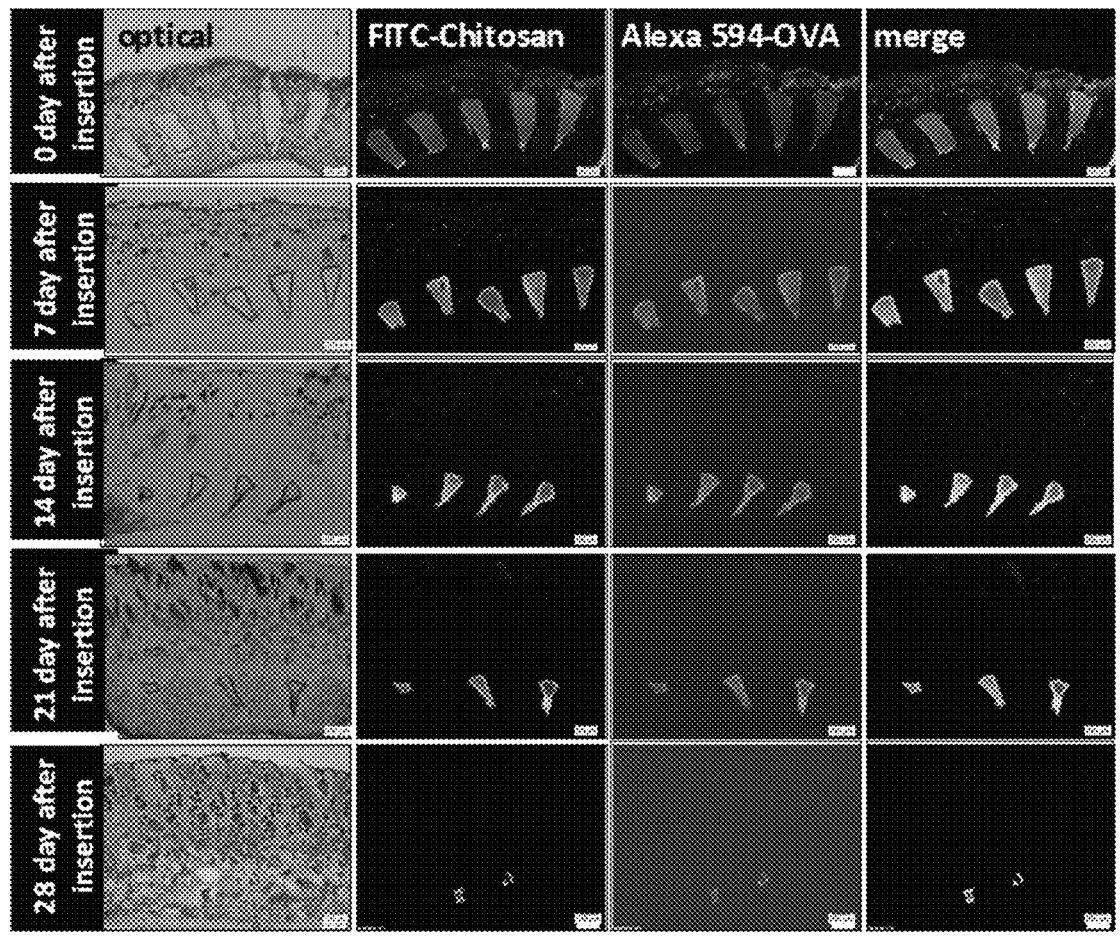
FIG. 12 shows histological section images of the microneedle insertion sites at 1 day, 1 week, 2 week, 3 week, and 4 week after application.

FIG. 12 shows fluorescent image of skin section with embedded chitosan microneedles. Each column from top to bottom represents skin section at the first (day 0), $7^{th}$, $14^{th}$, $21^{th}$ and $28^{th}$-day after insertion, respectively; each row from left to right represents the skin section under a light microscope, stained with FITC-Chitosan, Alexa 594-OVA, and the merged florescent images, respectively. With reference to FIG. 12, the results show that the chitosan microneedle is degraded in the rat with time increasing. The microneedle still can be observed on the $28^{th}$-day after insertion.

Figure 13A:
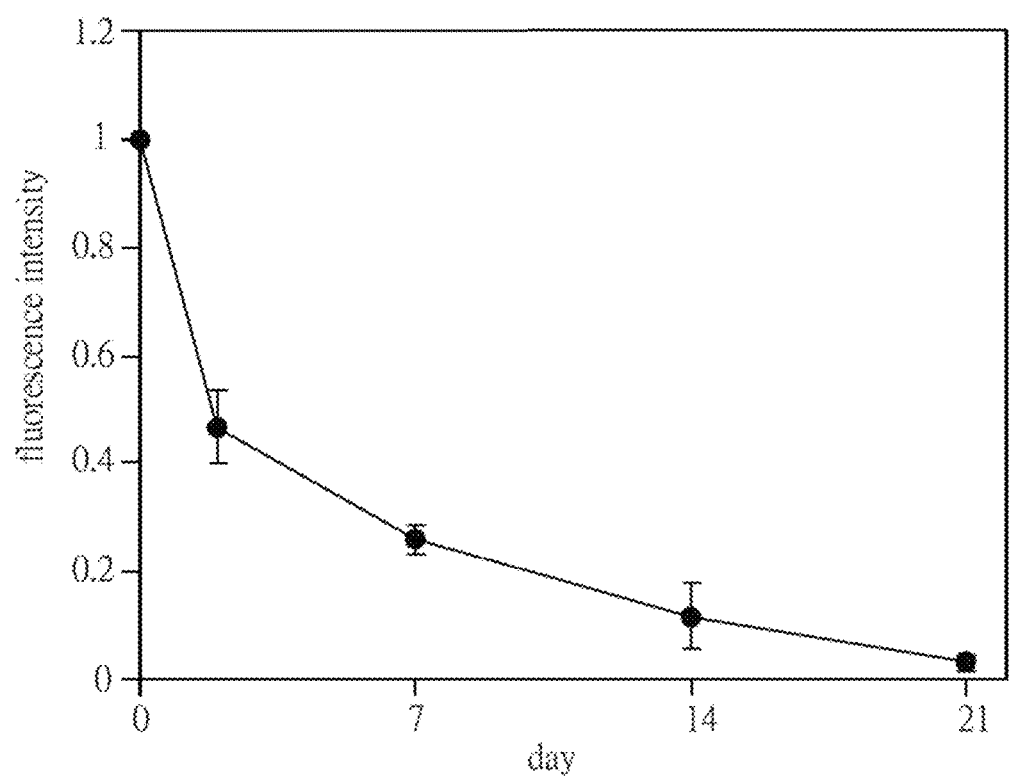
FIG. 13A shows relative fluorescence intensity of ovalbumin (OVA) in rat's body.
Figure 13B:
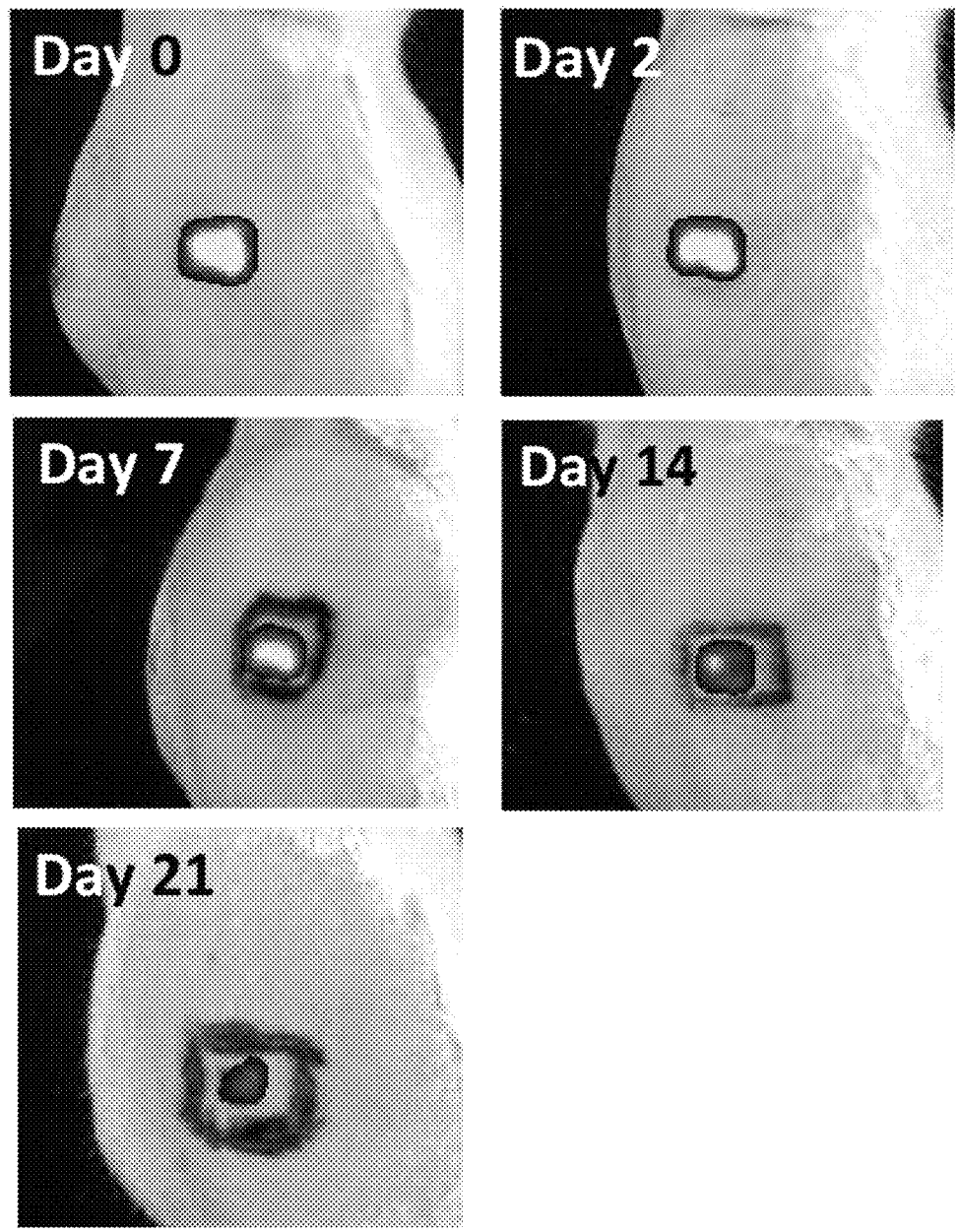
FIG. 13B shows in vivo imaging system (IVIS) images of SD rats after insertion of OVA-loaded chitosan microneedles at different time points.

We also observe release of ovalbumin (OVA) from embedded chitosan microneedles in the SD rat by IVIS system. With reference to FIG. 13A and FIG. 13B, FIG. 13A shows fluorescence intensity of OVA in rats, and FIG. 13B shows fluorescent images of OVA in rats in a time course experiment. At Day 2 post insertion, the OVA antigen release percentage is about 50%. For the next three weeks (7 days, 14 days, and 21 days), a slowly release of the antigen in a small amount is found. Such phenomena may be helpful to induce a secondary immune response or an anamnestic response.

Through the results showed above, the substance delivery device of the present embodiment has been demonstrated to be able to release the substances it carried in a sustained manner.

Experiment 5

Adjuvant Effect of Chitosan Administered Through Microneedles 4-week-old SD rats are divided into four groups. Rats of the first three groups are injected with saline, OVA, and chitosan hydrogel loaded with OVA by intramuscular inoculation, respectively. The fourth group is administrated with OVA through the microneedle patch of the present embodiment. In detail, the SD rat is weighed, anesthetized, and shaved. 200 µl of saline is injected into the thigh of each SD rat of the first group ("IM saline" group). 500 µg of OVA in the same volume are injected into the thigh of each SD rat of the second group ("IM-OVA" group). 200 µl of chitosan hydrogel loaded with 500 µg of OVA (mixed in the same ratio as the microneedle patch) are injected into the thigh of each SD rat of the third group ("IM-OVA+CS" group). A microneedle patch encapsulating 200 µg of OVA is applied the each SD rat of the fourth group ("MN-OVA" group). The blood of each SD rat of each group sampled at the 0, $2^{nd}$ and $4^{th}$ week after injection is centrifuged for 5 minutes at 3000 rpm to separate serum from blood cells in the plasma. IgG levels in the collected serum are then evaluated by ELISA. The result is shown in FIG. 14.

Figure 14:
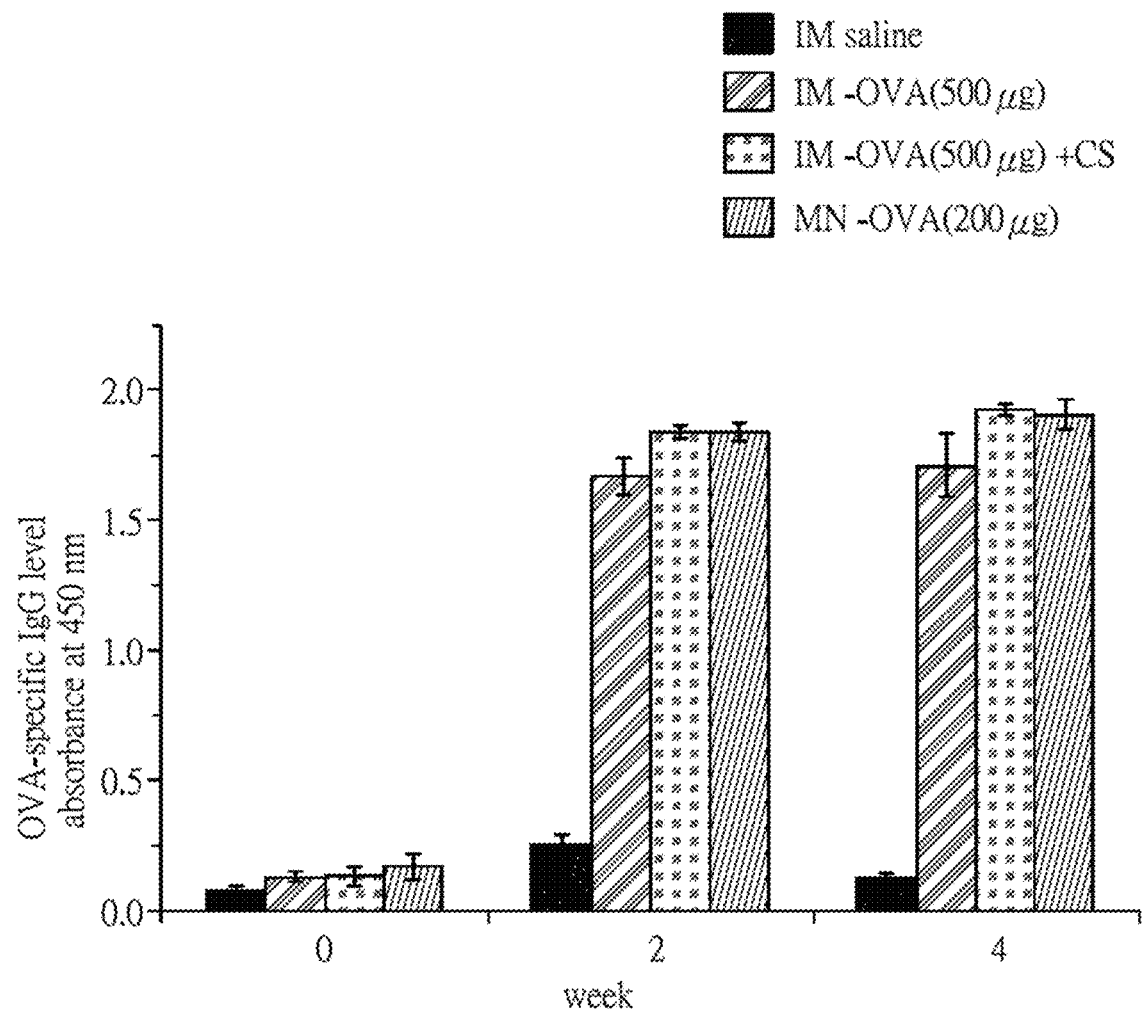
FIG. 14 shows OVA-specific IgG antibody levels of rats after a single dose of OVA antigen: non-immunized group (IM saline), intramuscularly immunized (IM-OVA, 500 µg OVA and IM-OVA+CS, 500 µg OVA), and microneedle-immunized (MN-OVA, 200 µg OVA)

FIG. 14 shows the OVA-specific IgG levels of the rats after immunization with OVA. The rats in IM saline group are shown that no significant immune response is induced. Two weeks after injection, the MN-OVA group can generate an equivalent OVA-specific IgG level to the IM-OVA+CS group, and the OVA-specific IgG level of the IM-OVA group is much lower than the MN-OVA and IM-OVA+CS group. The results demonstrate that chitosan microneedle has an adjuvant effect. In addition, a small amount of antigen (200 µg of OVA) encapsulated by chitosan microneedles can induce proper immune response when being administered through the microneedle patch of the present embodiment. Compared to that of the IM-OVA+CS group, which uses a higher dosage of vaccine (500 µg of OVA), the results of the MN-OVA group demonstrate that the microneedle patch of the present embodiment is advantageous for saving the amount of vaccines in practical use.

Experiment 6

Immunization of Mice with Influenza Vaccines Encapsulated in the Microneedle Patch 6-week-old ICR mice are divided into four groups. Mice of the first three groups are injected with saline, H1N1 inactivated viruses, and chitosan hydrogel loaded with H1N1 inactivated viruses by intramuscular inoculation. The mice of the fourth group are administrated with H1N1 inactivated viruses through the microneedle patch of the present embodiment. In detail, the ICR mice is weighed, anesthetized, and shaved. 50 µl of saline are injected into the thigh of each mouse of the first group ("IM saline" group). 500 of 256 HA H1N1 inactivated viruses are injected into the thigh of each mouse of the second group ("IM-vaccine" group). 50 µl of chitosan hydrogel loaded with 256 HA H1N1 inactivated viruses (mixed in the same ratio as the microneedle match ("IM-vaccine+CS" group). A microneedle patch encapsulating 256 HA H1N1 inactivated viruses is applied to each mouse of the fourth group ("MN-vaccine" group). The blood sampled from the cheek of each ICR mouse of each group at the 0, $2^{nd}$, $4^{th}$, $6^{th}$, $8^{th}$, $10^{th}$ week after injection is centrifuged for 5 minutes at 3000 rpm to separate serum from blood cells in the plasma. IgG levels of the collected serum are then evaluated by ELISA. The result is shown in FIG. 15.

Figure 15:
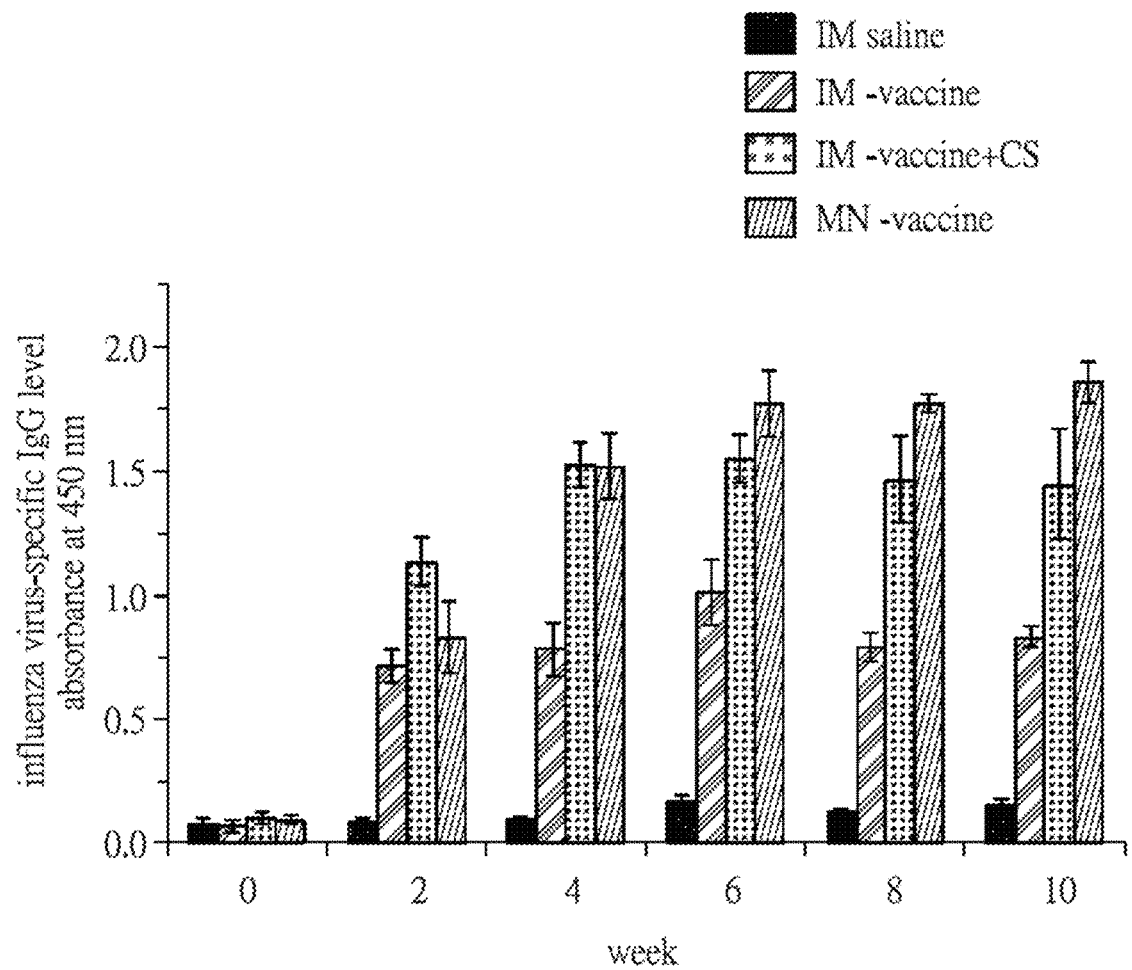
FIG. 15 shows influenza virus-specific IgG antibody levels of mice after a single dose of inactivated influenza WSN virus vaccine (256 HA): non-immunized group (IM saline), intramuscularly immunized (IM-vaccine and IM-vaccine+CS), and microneedle-immunized (MN-vaccine)
Figure 16:
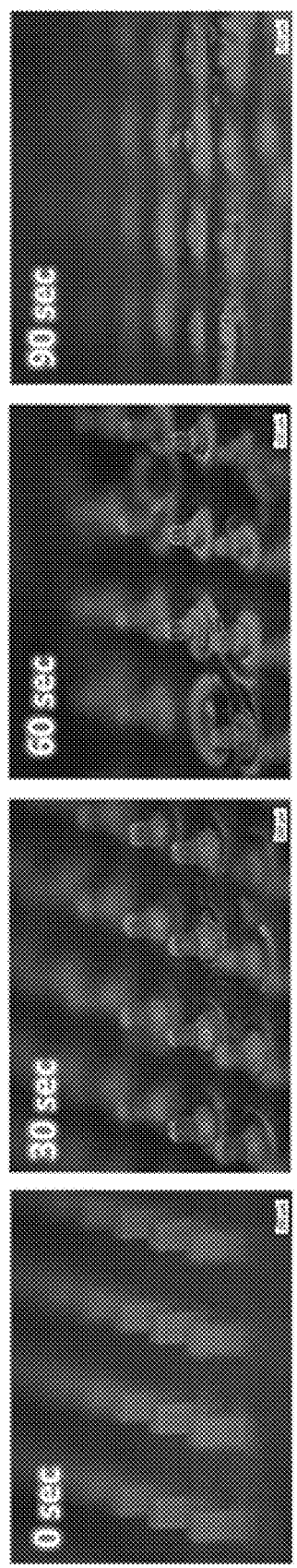
FIG. 16 shows the stereomicroscope images of the supporting structures which were made by different materials: PVP/PVA supporting structures (PVP/PVA), hyaluronic acid supporting structures (HA), γ-poly-glutamic acid supporting structures (γ-PGA, gamma-PGA)
Figure 16:
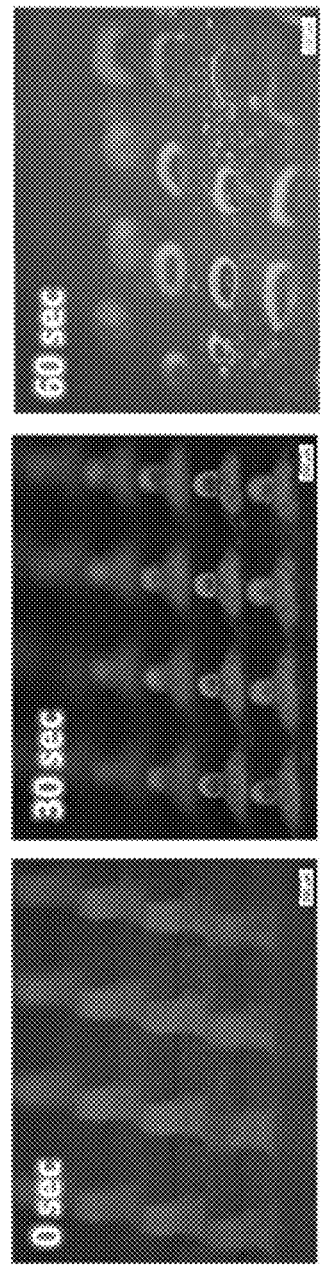
Figure 16:
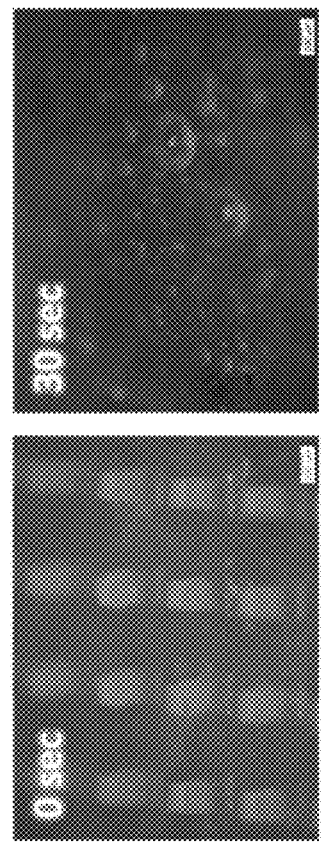
Figure 17A:
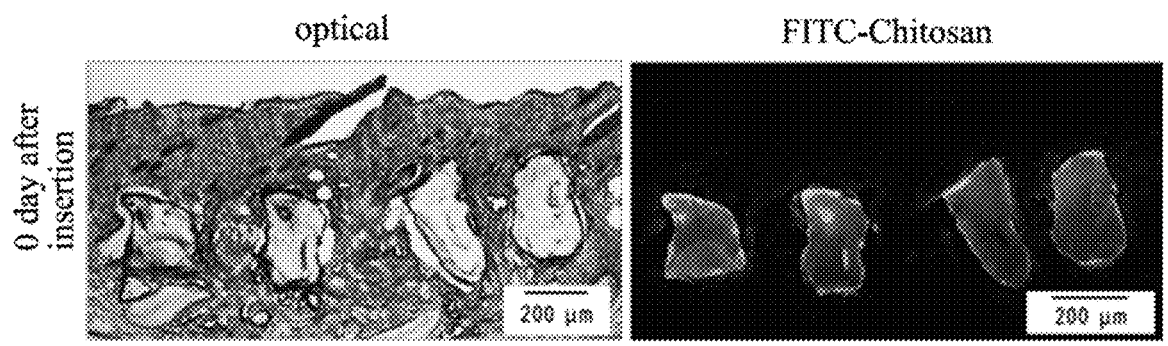
FIG. 17A-17B shows histological section images of the microneedle insertion sites at 1 day after application.
Figure 17B:

FIG. 15 shows influenza virus-specific IgG antibody levels of mice evaluated by ELISA. With reference to FIG. 15, two weeks from the injection, the mice in the IM-vaccine+CS group are found to generate the highest level of IgG antibody, and the mice in the IM-vaccine group are found to generate an equivalent amount of IgG as the mice in the MN-vaccine group. However, chitosan microneedles are slowly degraded and H1N1 inactivated viruses are found to be released in a sustained manner until the fourth week. And, after six weeks from injection, IgG levels of the mice in the MN-vaccine group are found to be substantially higher than those of the mice in the other two groups.

Furthermore, when each mouse in each group is injected with a single dose of vaccine, the mice in the IM-vaccine group are found to generate an apparently lower level of IgG antibody than the mice in other groups do. In other words, the microneedle patch uses chitosan as the material for carriers, and chitosan can simultaneously act as an adjuvant. In addition, the transdermal delivery of vaccines through the microneedle patch of the present embodiment is found to be able to induce the mice to generate a high level of IgG antibody for at least 10 weeks after injection (as shown in the result of the MN-vaccine group), and is therefore able to effectively protect the individual against the challenge of the environmental pathogen for a long period of time.

Experiment 7

Dissolution Test of Supporting Structures

FIG. 16 shows the stereomicroscope images of the supporting structures which were made by different materials. 40 μl of deionized water is added onto the surface of the supporting structures. After a specific time points (30, 60, or 90 sec), the added water is removed by dabbing the surfaces of the samples with filter paper. The morphology change of the sample was examined using a stereomicroscope. As shown in FIG. 16, the PVP/PVA supporting structures (PVP/PVA) were almost totally dissolved by water after 90 sec. The hyaluronic acid supporting structures (HA) were almost totally dissolved by water after 60 sec. The γ-poly-glutamic acid supporting structures (γ-PGA) were almost totally dissolved by water after 30 sec. Therefore, the solubility of the supporting structures is different based on the materials of the supporting structures. The solubility of γ-PGA supporting structures is better than HA supporting structures. The solubility of HA supporting structures is better than PVP/PVA supporting structures.

Experiment 8

In Vivo Insertion 4-week-old Sprague-Dawley rats are anesthetized and shaved. Rats are sacrificed on the first (day 1) day after microneedle insertion, respectively. The skin where the microneedles are inserted is collected with size 1 cm×1 cm, and the skin is then embedded for frozen sections to observe the result of insertion of chitosan microneedles in the skin. The insertion result of the chitosan microneedles in the rat skin is shown as FIG. 17A-17B.

FIG. 17A shows images of skin section after insertion of FITC-chitosan microneedles with γ-poly-glutamic acid supporting structures (γ-PGA). Row from left to right represents the skin section under a light and a fluorescent microscope. With reference to FIG. 17A, the results show that the γ-poly-glutamic acid supporting structures can provide enough mechanical strength to fully insert chitosan microneedleinto the rat skin.

FIG. 17B shows images of skin section after insertion of FITC-chitosan microneedles with hyaluronic acid supporting structures (HA). Row from left to right represents the skin section under a light and a fluorescent microscope. With reference to FIG. 17B, the results show that the hyaluronic acid supporting structures can provide enough mechanical strength to fully insert chitosan microneedle into the rat skin.

Through the results showed above, the substance delivery device of the present embodiment has been demonstrated to be able to fully insert into skin.

The above experiments have shown that the substance delivery device of the present invention is advantageous for gradually releasing the substance in a sustained manner and make the substance to be effective for a longer period of time. Because the polymer utilized in the substance delivery device of the present invention may be all bio-compatible, the substance delivery device, when it is applied to an individual, may not cause any adverse effects to the functions of its organs and the life of the individual.

As mentioned above, the substance delivery device of the present invention applies a combination of dissolvable supporting structures and carriers to make a delivery system capable of delivering substances through tissues, especially through skin or mucosa (i.e., transdermal or transmucosal delivery). Meanwhile, the present invention also provides a substance delivery device for sustained release of substances. Furthermore, the dissolvable supporting structure of the substance delivery device of the present invention is able to be dissolved by the body fluid and/or interstitial fluid in the skin The carriers are then left in the inserted skin and swell and degrade to gradually release the drug in a sustained manner. Accordingly, the effectiveness of the substances may last longer. More importantly, compared to the traditional microneedle patches which are necessary to attach on the skin for quite a long time to maintain its effectiveness, the substance delivery device of the present invention and the method thereof are not necessary to attach the substrate on the skin during the releasing of the drug, and it significantly decreases the contacting time to the skin. Therefore, the possibility to induce symptoms of allergy, such as itching and skin rashness, is diminished and patients' discomfort is also reduced.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A substance delivery device comprises:

a dissolvable substrate configured to be attached to a tissue;

a plurality of dissolvable supporting structures disposed on the dissolvable substrate, wherein each of the dissolvable supporting structures is a square and straight column, and each of the dissolvable supporting structures has a section whose area remains the same along a longitudinal axis of the dissolvable supporting structures;

a plurality of degradable carriers disposed on the dissolvable supporting structures and encapsulating a plurality of first substances which are configured to be delivered into the tissue; and an adhesive, which is disposed on each of the dissolvable supporting structures to stick with each of the corresponding degradable carriers;

wherein the dissolvable supporting structures are configured to be dissolved in the tissue after the degradable carriers and the dissolvable supporting structures are inserted into the tissue, so as to make the dissolvable substrate separate from the degradable carriers, and the degradable carriers are configured to swell and degrade to release the first substances into the tissue when the degradable carriers are left in the tissue, wherein the dissolvable substrate and the dissolvable supporting structures are integrally formed, wherein the dissolvable substrate and the dissolvable supporting structures have the same material, and the material includes γ-poly-glutamic acid, hyaluronic acid, starch, gelatin, or their combinations.

2. The substance delivery device according to claim 1, wherein a plurality of second substances are encapsulated in the dissolvable supporting structures and configured to be delivered into the tissue, and the second substances are the same as the first substances encapsulated in the degradable carriers.

3. The substance delivery device according to claim 1, wherein a plurality of second substances are encapsulated in the dissolvable supporting structures and configured to be delivered into the tissue, and the second substances are different from the first substances encapsulated in the degradable carriers.

4. The substance delivery device according to claim 1, wherein the degradable carriers include a material capable of melting after exposure to a radiation.

5. The substance delivery device according to claim 1, wherein the degradable carriers include chitosan, chitin, silk, carboxymethyl cellulose, chondroitin, collagen, gelatin, polycaprolactone, poly(methyl vinyl ether-maleic anhydride), polyacrylic acid, 2-hydroxyethyl methacrylate, N,N-dimetyl acrylamide, maltose, hyaluronic acid, polylactic acid, polyglycolic acid, poly(lactic-co-glycolic acid), or their combinations.

6. A substance delivery method applied with a substance delivery device, wherein the substance delivery device includes a dissolvable substrate, a plurality of dissolvable supporting structures, a plurality of degradable carriers and an adhesive, the dissolvable supporting structures are disposed on the dissolvable substrate, the dissolvable substrate and the dissolvable supporting structures are integrally formed with the same material, the degradable carriers are disposed on the dissolvable supporting structures and encapsulate a plurality of first substances which are configured to be delivered into the tissue, the adhesive is disposed on each of the dissolvable supporting structures to stick with each of the corresponding degradable carriers, each of the dissolvable supporting structures is a square and straight column, each of the dissolvable supporting structures has a section whose area remains the same along a longitudinal axis of the dissolvable supporting structures, the substance delivery method comprising the following steps:

adhering the dissolvable substrate to a tissue so as to make the degradable carriers and the dissolvable supporting structures are inserted into the tissue; and after the degradable carriers and the dissolvable supporting structures are inserted into the tissue, dissolving the dissolvable supporting structures in the tissue so as to make the degradable carriers separate from the dissolvable substrate and swelling and degrading the degradable carriers to release the first substances into the tissue when the degradable carriers are left in the tissue, wherein the dissolvable supporting structures includes γ-poly-glutamic acid and hyaluronic acid.

7. The substance delivery device according to claim 6, further comprising:

providing water or solution to the tissue or its surrounding.

8. The substance delivery device according to claim 6, wherein the dissolvable supporting structures further include starch, gelatin, or their combinations.

9. The substance delivery device according to claim 6, wherein a plurality of second substances are encapsulated in the dissolvable supporting structures, and the second substances are the same as the first substances encapsulated in the degradable carriers.

10. The substance delivery device according to claim 6, wherein a plurality of second substances are encapsulated in the dissolvable supporting structures, and the second substances are different from the first substances encapsulated in the degradable carriers.

11. The substance delivery device according to claim 6, wherein the degradable carriers include a material capable of melting after exposure to a radiation.

12. The substance delivery device according to claim 6, wherein the degradable carriers include chitosan, chitin, silk, carboxymethyl cellulose, chondroitin, collagen, gelatin, polycaprolactone, poly(methyl vinyl ether-maleic anhydride), polyacrylic acid, 2-hydroxyethyl methacrylate, N,N-dimetyl acrylamide, maltose, hyaluronic acid, polylactic acid, polyglycolic acid, poly(lactic-co-glycolic acid), or their combinations.

13. The substance delivery device according to claim 6, wherein the tissue includes skin, mucosa, cornea or sclera.

14. A substance delivery device comprises:

a dissolvable substrate configured to be attached to a tissue;

a plurality of dissolvable supporting structures disposed on the dissolvable substrate, wherein each of the dissolvable supporting structures is a square and straight column, each of the dissolvable supporting structures has a section whose area remains the same along a longitudinal axis of the dissolvable supporting structures, a height of the dissolvable supporting structures ranges from 600 μm to 900 μm and a width of the dissolvable supporting structures ranges from 200 μm to 400 μm;

a plurality of degradable carriers disposed on the dissolvable supporting structures and encapsulating a plurality of first substances which are configured to be delivered into the tissue; and an adhesive, which is disposed on each of the dissolvable supporting structures to stick with each of the corresponding degradable carriers;

wherein a height of the degradable carriers ranges from 400 μm to 800 μm and a width of one end of the degradable carriers connected to the dissolvable supporting structures ranges from 200 μm to 400 μm; and wherein the dissolvable supporting structures are configured to be dissolved in the tissue after the degradable carriers and the dissolvable supporting structures are inserted into the tissue, so as to make the dissolvable substrate separate from the degradable carriers, and the degradable carriers are configured to swell and degrade to release the first substances into the tissue when the degradable carriers are left in the tissue, wherein the dissolvable substrate and the dissolvable supporting structures are integrally formed, wherein the dissolvable substrate and the dissolvable supporting structures have the same material, and the material includes γ-poly-glutamic acid, hyaluronic acid, starch, gelatin, or their combinations.

15. The substance delivery device according to claim 1, wherein the dissolvable substrate is configured to cover the tissue for less discomfort for user.

16. The substance delivery method according to claim 6, wherein the dissolvable substrate is configured to cover the tissue for less discomfort for user.

17. The substance delivery device according to claim 14, wherein the dissolvable substrate is configured to cover the tissue for less discomfort for user.

* * * * *